(12) United States Patent
Sugita

(10) Patent No.: US 7,430,039 B2
(45) Date of Patent: Sep. 30, 2008

(54) SENSOR

(75) Inventor: Mitsuro Sugita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 367 days.

(21) Appl. No.: 10/527,840

(22) PCT Filed: Oct. 10, 2003

(86) PCT No.: PCT/JP03/13073

§ 371 (c)(1),
(2), (4) Date: Oct. 31, 2005

(87) PCT Pub. No.: WO2004/034527

PCT Pub. Date: Apr. 22, 2004

(65) Prior Publication Data

US 2006/0123900 A1    Jun. 15, 2006

(30) Foreign Application Priority Data

Oct. 11, 2002    (JP)    ............................. 2002-299153

(51) Int. Cl.
*G01N 33/48*    (2006.01)
*G01N 21/00*    (2006.01)
*H01L 49/00*    (2006.01)
*H01S 3/08*    (2006.01)

(52) U.S. Cl. .................. 356/39; 356/72; 435/287.1; 257/414; 257/415; 257/467; 372/92; 372/97

(58) Field of Classification Search .................. 356/39, 356/72; 257/414, 415, 467; 435/287.1; 372/92, 372/97

See application file for complete search history.

(56) References Cited

U.S. PATENT DOCUMENTS

| | | | |
|---|---|---|---|
| 5,353,262 A | 10/1994 | Yakymyshyn et al. | 367/149 |
| 5,500,540 A | 3/1996 | Jewell et al. | 257/82 |
| 5,754,333 A | 5/1998 | Fulbert et al. | 359/330 |
| 5,892,586 A | 4/1999 | Thony et al. | 356/437 |
| 6,165,335 A | 12/2000 | Lennox et al. | 204/403 |
| 6,327,287 B1 | 12/2001 | Kner et al. | 372/43 |
| 2002/0048301 A1 | 4/2002 | Wang et al. | 372/45 |
| 2002/0153805 A1 | 10/2002 | Smith et al. | 310/311 |

FOREIGN PATENT DOCUMENTS

| | | |
|---|---|---|
| JP | 10-284806 | 10/1998 |
| JP | 10-337173 | 12/1998 |
| WO | WO 99/37996 | 7/1999 |
| WO | WO 01/40757 | 6/2001 |
| WO | 01/88511 | 11/2001 |
| WO | WO 02/071013 | 9/2002 |

*Primary Examiner*—Evan Pert
(74) *Attorney, Agent, or Firm*—Fitzpatrick, Cella, Harper & Scinto

(57) ABSTRACT

Sensors are provided which enable detection with a high sensitivity in microchemistry and biochemical analysis by using devices integrated into a compact configuration and can be freely disposed on desired positions of a channel to perform detection.

A measuring apparatus for detecting information and outputting light according to the information, the apparatus comprising: an active layer for emitting light and a micro-optical cavity, wherein light emission is limited in the active layer due to the influence of the selection of a photoelectromagnetic field mode, the selection is made by the micro-optical cavity, the light emission and a degree of selection of a photoelectromagnetic field mode is changed according to an environmental condition of the micro-optical cavity, so that the light emission is changed and the environmental condition is measured according to a change in the light emission.

21 Claims, 15 Drawing Sheets

FIG. 16A
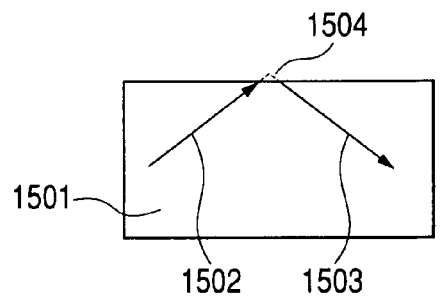
FIG. 16B
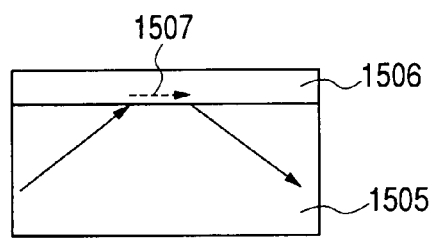
FIG. 16C
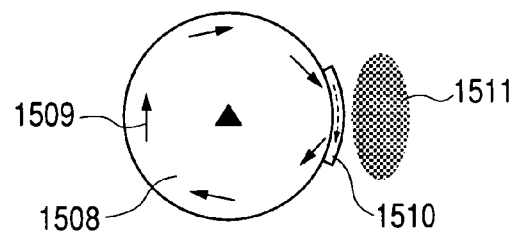
FIG. 17A   FIG. 17B   FIG. 17C
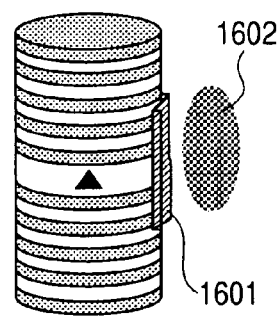 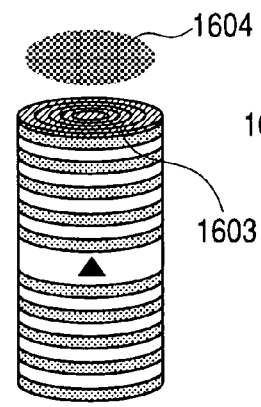 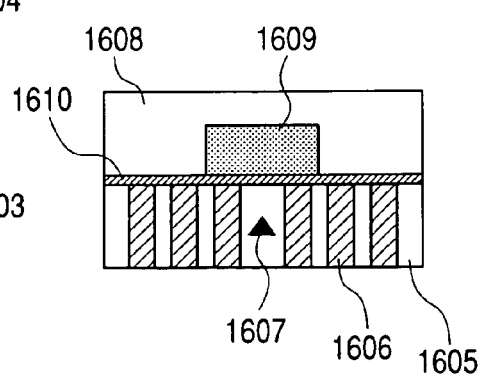

SENSOR

TECHNICAL FILED

The present invention relates to a sensor for reading a concentration of a substance flowing into a channel of a micro analysis system (μ-TAS), a micro pressure distribution and temperature distribution, and biological and genetic information. Further, the present invention relates to a data transmitter which transmits and processes detected information with high efficiency.

BACKGROUND ART

In recent years techniques for performing analysis with smaller systems have been developed in chemical and biochemical fields. A typical example is a μ-TAS system using a microchannel. Separation/mixing, reaction and so on have been performed with channels smaller than conventional ones. Moreover, a detecting element called DNA chip for reading biological and genetic information has been developed with the development of biotechnology and bioindustry.

Further, as three-dimensional micromachining develops in recent years, attention has been given to systems in which a small channel, a liquid device such as a pump and valve, and a sensor are integrated on a substrate made of a material selected from the group consisting of glass and silicon, and chemical analysis is performed on the substrate. These systems are called a miniaturizing analysis system, a μ-TAS (Micro Total Analysis System) or Lab on a Chip. By reducing the size of a chemical analysis system, a reactive volume can be reduced and an amount of a sample can be largely reduced. Besides, analysis time can be shortened and the power consumption of the whole system can be reduced. Furthermore, a smaller system raises expectations for the lower cost thereof. Since the μ-TAS can miniaturize the system, reduce the cost, and remarkably shorten analysis time, it is expected that μ-TAS will be applied to a medical field including home care and bedside monitoring and a biotechnological field including DNA analysis and proteome analysis.

For example, a microreactor is disclosed in which a series of biochemical experiments can be performed by a combination of several cells (Japanese Patent Application Laid-Open No. 10-337173). In the series of experiments, after a solution is mixed and reaction is performed, quantitative analysis is performed and then separation is performed. FIG. 11 schematically shows the concept of a microreactor 11. The microreactor 11 has a separate reaction chamber which is covered tightly with a flat plane on a silicon substrate. A reservoir cell 12, a mixture cell 13, a reaction cell 14, a detection cell 15, and a separation cell 16 are combined in the reactor. By forming a number of reactors on the substrate, a number of biochemical reactions can be performed in parallel. Not only simple analysis but also substance synthesis such as protein synthesis can be performed on cells.

Such a μ-TAS system and a biochip finally require a detecting step after operations including reaction are performed. Detection with light has been used as a method less affecting an analyte with higher accuracy due to its non-contact property and nonresponsiveness. For example, measuring methods have been used which include a measuring method of adding a fluorescence label to an analyte and emitting light from an exciting light source to detect fluorescence, a measuring method of irradiating an analyte with light from a light source to measure the intensity of transmitted light, and a method of bringing a prism close to an analyte, emitting light from a light source, and measuring loss of total reflected light.

However, the method using a fluorescence label raises a problem of congeniality between an analyte and a label, so that a desired label, that is a label with a high sensitivity may not be used. Further, excitation light and fluorescence have different wavelengths in this method. Although degradation is less caused by intensive excitation light serving as noise components, efficiency of generating fluorescence serving as signal components is hard to increase. Therefore, it is difficult to increase an overall S/N ratio.

According to the method of measuring a transmittance and an absorbance by using transmitted light, when an analyte has a low transmittance, that is when a measured substance which is included in a detected fluid has a high concentration, a signal is reduced due to a small quantity of transmitted light, resulting in a low S/N ratio. When the concentration of a measured substance is reduced to improve the S/N ratio, the original signal is reduced and thus the S/N ratio is degraded. Further, although measurements are less affected by light, light directly crosses a detected fluid. Thus, measurements are prone to being affected by heat generation or photoreaction, thereby limiting a quantity of usable light.

According to the method of measuring a loss of total reflected light, it is possible to use a larger quantity of light as compared with transmitted light. However, light having a change (loss) to be detected and irradiated light are equal in wavelength, so that a detector requires quite a large dynamic range. Namely, it is not possible to precisely measure a small loss caused by slight reaction or the like in a microchannel.

The present invention is devised to solve the above problem of the conventional technique and provides a sensor and a measuring apparatus whereby in microchemistry and biochemical analysis of a μ-TAS system, a bioanalysis chip, and so on using a microchannel, detection can be performed with a high sensitivity by using devices integrated into a compact configuration, and detection can be freely performed on a desired position of a channel. Moreover, according to the present invention, microcavity laser is applied to provide a portable tester.

DISCLOSURE OF THE INVENTION

According to an aspect of the present invention, there is provided a sensor for detecting information and outputting light according to the information, the sensor wherein it comprises a micro-optical cavity for changing a degree of selection of a photoelectromagnetic field mode according to an environmental condition of the cavity; and an active layer in which light emission is limited by influence of the selection of a photoelectromagnetic field mode, wherein the light emission is changed according to a change in the environmental condition.

According to another aspect of the present invention, there is provided a sensor array comprising the sensors of claim 1 arranged juxtapositionally in one- or two-dimensional array and outputting a signal of juxtapositional lights outputted from the sensors according to a plurality of environment information corresponding to positions of the sensors.

According to still another aspect of the present invention, there is provided a method for acquiring sensor information, wherein the sensor array of claim 16 is used and the signal of juxtapositional lights from the sensor array is detected by an area sensor.

According to a further aspect of the present invention, there is provided a sensor using a microcavity laser, wherein one of two supporting substances capable of making specific binding with a substance to be detected is supported on a peripheral portion of the micro-optical cavity, and a specific binding state of the substance to be detected with the supporting substance is detected based on information about laser oscillation state of detected laser. Further, the present invention relates to a sensor system, wherein the sensors are juxtapositionally arranged on a common substrate and plural kinds of substances to be detected are juxtapositionally detected by using a plurality of microcavity lasers juxtapositionally arranged.

According to a further aspect of the present invention, there is provided a sensor comprising a micro-optical cavity of a microcavity laser and a probe for generating mechanical deformation on the micro-optical cavity, wherein a state of the mechanical deformation is detected by measuring a change in laser oscillation state, the change being caused by deformation of the micro-optical cavity through the probe.

BRIEF DESCRIPTION OF THE DRAWINGS

FIGS. 16A, 16B and 16C are schematic views showing an example of the configuration of a sensor using metal surface plasmon according to Example 10;

FIGS. 17A, 17B amnd 17C are schematic views showing an example of another configuration of a sensor using metal surface plasmon according to Example 10;

BEST MODE FOR CARRYING OUT THE INVENTION

Figure 1A:
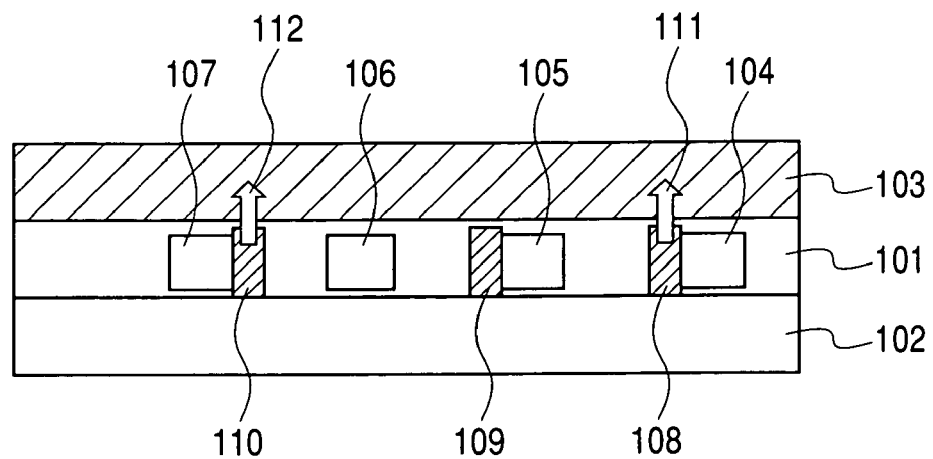
FIGS. 1A and 1B are schematic sectional views each showing the configuration of a fluid component detector according to Example 1 which uses a sensor of the present invention.

The following will describe a preferred embodiment of the present invention.

A sensor according to the present invention is preferably used to detect information other than light.

The sensor of the present invention is preferably disposed in a channel for flowing a fluid or near the channel, and the environmental condition is preferably changed according to a solution flowing in the channel or a dissolved substance or solvent of the solution. The channel is preferably a microchannel having a dimension of 10 µm or more and a solution flowing in the channel preferably forms a laminar flow on a predetermined position. Further, the environmental condition is more preferably selected from the group consisting of a change in refractive index, light absorption, light scattering, a temperature change, and slight deformation of the sensor. The change in refractive index may depend upon a concentration of the solvent or a temperature of the solution. The light adsorption may depend upon a concentration of the dissolved substance. The temperature change may be caused by heat generated by a chemical reaction of the solution and/or the dissolved substance. The sensor may respond to vibration caused by expansion and shrinkage resulting from a collision of the dissolved substance or a chemical reaction of a substance in the solution. The slight deformation of the sensor may appear due to a pressure change caused by expansion and shrinkage resulting from a change in a flow rate of the solution or a chemical reaction of a substance in the solution. Alternatively, the slight deformation of the sensor may appear due to a pressure change caused by expansion and shrinkage resulting from a change in a flow rate of the solution or a chemical reaction of a substance in the solution.

A surrounding part of the micro-optical cavity in the sensor of the present invention may be modified by an antigen or an antibody.

The sensor of the present invention may further comprises a probe for generating mechanical deformation on the micro-optical cavity.

The sensor of the present invention may further comprises a metal thin film between the micro-optical cavity and a detected substance.

In the sensor of the present invention, a kind of a substance to be detected may be detected according to a change in a laser oscillation mode of the microcavity a peripheral portion of which supports plural kinds of the supporting substance, the supporting substances corresponding to plural kinds of the substance to be detected. In this case, the probe may support one of two supporting substances capable of making specific binding with the substance to be detected, and modulation of mechanical deformation of the micro-optical cavity through the probe may be detected from a change in the laser oscillation state, which change is based on a mechanical resistance against ambient fluid and/or a change in weight of the probe by the specific binding.

In the present invention, light is outputted according to information. The information is preferably information other than light.

In a normal sensor, an electrical change, that is a change in current or voltage is used as output. Although such an electrical output is secondarily converted into light to perform optical communication in some cases, the sensor of the present invention is characterized in that the primary output of the sensor is light.

In the present invention, an active layer for emitting light indicates an active layer in a semiconductor light-emitting device such as a semiconductor laser. Positive electric charge and negative electric charge (carrier) emits light and are recoupled with each other on a diode PN junction of the semiconductor light-emitting device. The region is called an active region. The region is normally formed like a layer and thus the region is indicated as an active layer. Therefore, an "active layer" may indicate an active region in the present specification.

The micro-optical cavity of the present invention is represented as a microcavity or a microcavity in the field of optical devices. Further, a "microdisk cavity" indicates a micro-disk cavity laser and a microsphere cavity laser.

A photoelectromagnetic field mode is preferably a natural mode of vibration in an electromagnetic field regarding light of an optical mode or an optoelectronic magnetic field mode.

Further, as to the natural mode of vibration, vibration includes two variables for a space and time. Thus, two characteristics of a space mode and a time mode are present. The time mode indicates selection of a wavelength of light, and the space mode indicates the distribution of light intensity (to be precise, complex amplitude has a phase) inside and outside the cavity. In the present invention, "confinement of light" preferably uses only a space mode in which a part with intensive light is concentrated in a narrow region, in terms of the space mode.

In the present invention, a plurality of optoelectronic magnetic field modes are present in a normal condition. When the microcavity is reduced in size, a single mode is present in principle and light is emitted only in a predetermined direction. In reality, coupling is slightly made to, for example, a mode emitting unnecessary light diverging widely around a cavity. The degree of undesirable leaked light is normally defined by a Q-factor (Quality factor) which is a physically defined quantity. This means that when a cavity of a value of a wavelength has Q of 1000, light leaks to the outside and disappears after making 1000 reciprocations. When a leakage quantity is completely 0 and only a single mode is actually used, laser has a threshold current of 0A. Since the threshold current is nA and μA in reality, some leaked light is present.

In the present invention, the specific examples of the environmental conditions of the microcavity include a refractive index of a substance making contact with the cavity, force (including a vibration and pressure) received from a substance making contact with the microcavity, and a temperature of a substance making contact with the microcavity.

In the present invention, the sensor preferably measures the environmental conditions as well as a change in light emission. The measurement of the environmental conditions is the object and the measurement of light or injected current for pumping can be used as a means.

For the sensor of the present invention, a microcavity LD is used. The microcavity LD has been already known. The present invention is characterized by using the microcavity LD to measure the environmental conditions. For example, the microcavity LD does not operate well in the event of a temperature change in some cases. The present invention is characterized by using such a phenomenon for a sensor such as a measuring apparatus.

In the present invention, the sensor is disposed in a channel for flowing a solution or in the neighborhood of the channel. "Neighborhood" is defined as follows:

(1) In the case of a refractive index of a substance making contact with the microcavity, the neighborhood indicates a range for sensing a photoelectromagnetic field. The range of a wavelength order, that is the upper limit is about 0.01 μm to about 10 μm in substance.
(2) In the case of force received from a substance making contact with the microcavity, the neighborhood indicates a conduction range of vibration and pressure. This range is varied with configurations and the upper limit is about 0.1 μm to about 10 mm.
(3) In the case of a temperature of a substance making contact with the microcavity, the neighborhood indicates a range of heat conduction. This range is varied with heat conductivities and thermal resistances and the upper limit is about 0.1 μm to about 10 mm.

Therefore, the neighborhood of 0 corresponds to the configuration of Example 2 in which a hole is formed on a channel and a microcavity is used as a wall of a channel.

In the present invention, a fluid flows into a channel and the fluid specifically includes a liquid and a gas. When a gas carries particles, a refractive index, a temperature, a concentration, and a vibration change as in the case of a liquid. Thus, the present invention is applicable to a gas which serves as a fluid flowing in the channel and carries particles.

As will be described below, with a microsensor using an ultralow-threshold laser of the microcavity according to the present invention, in microchemistry and biochemical analysis of a μ-TAS system, a bioanalysis chip and so on using a microchannel, detection can be performed with a high sensitivity by using devices integrated into a compact configuration, and a plurality of detectors can be freely disposed on desired positions of the channel on a flat surface. Moreover, a signal corresponding to detected information is subjected to parallel light output with an array of devices, so that parallel output can be directly processed and transmission can be performed with a simple configuration. Moreover, a portable tester can be also formed by applying the microcavity laser of the present invention.

EXAMPLES

Referring to examples, the present invention will be specifically described below. Hereinafter, LD denotes a microcavity laser diode.

Example 1

Figure 1B:
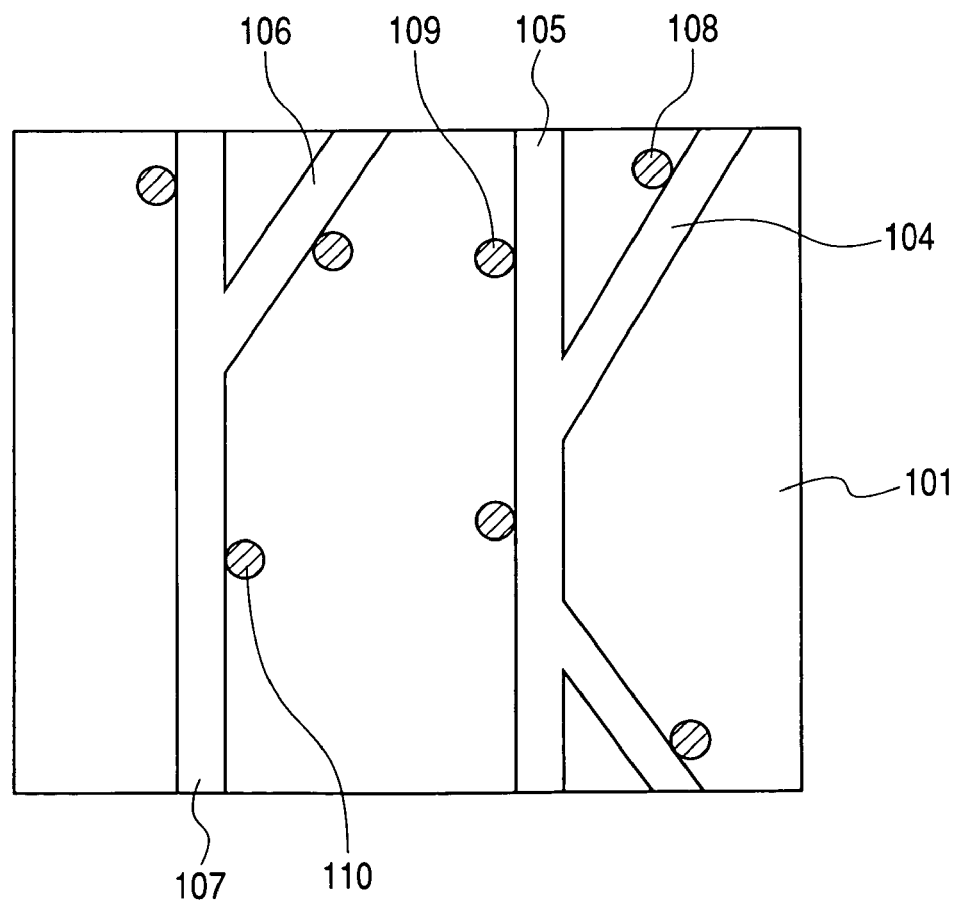

In the present example, the sensor of the present invention is applied to a fluid component detector. As shown in FIG. 1A, the fluid component detector includes three layers of an channel LD layer 101, a wiring layer 102, and a light-receiving layer 103 and channels. FIG. 1B is a schematic plan sectional view showing the LD layer 101.

The channels represented as 104, 105, 106 and 107 and LDs represented as 108, 109 and 110 are disposed in the same layer, that is the channel LD layer 101. Carriers are supplied to the LDs by the wiring layer 102, and light outputs 111 and 112 from the LDs are detected by the light-receiving layer 103 on the opposite side. Namely, the light-receiving layer 103 of the present example functions as an area sensor for detecting a light output signal from the sensor. In the present example, by using a CCD image sensor, the position of the LD emitting light is detected, the light quantity of the LD is detected for each of the LDs as an image, and the image is processed.

The microcavity LD of the present example is 1 to 10 μm in size. A used wavelength ranges from about 1.5 μm, which is near-infrared for optical communication, to about 300 nm from which little light passes through glass. For information, an ordinary surface-emitting laser is on the order of size that exceeds the size of the microcavity LD.

In the present example, the size of the channel in cross section, that is the width of the channel is about 10 μm. The width of the channel can be selected from 1 to several hundreds μm in consideration of fluid control techniques including the use of a laminar flow employed in so-called μ-TAS (Micro Total Analysis Systems) and so on.

Figure 2:
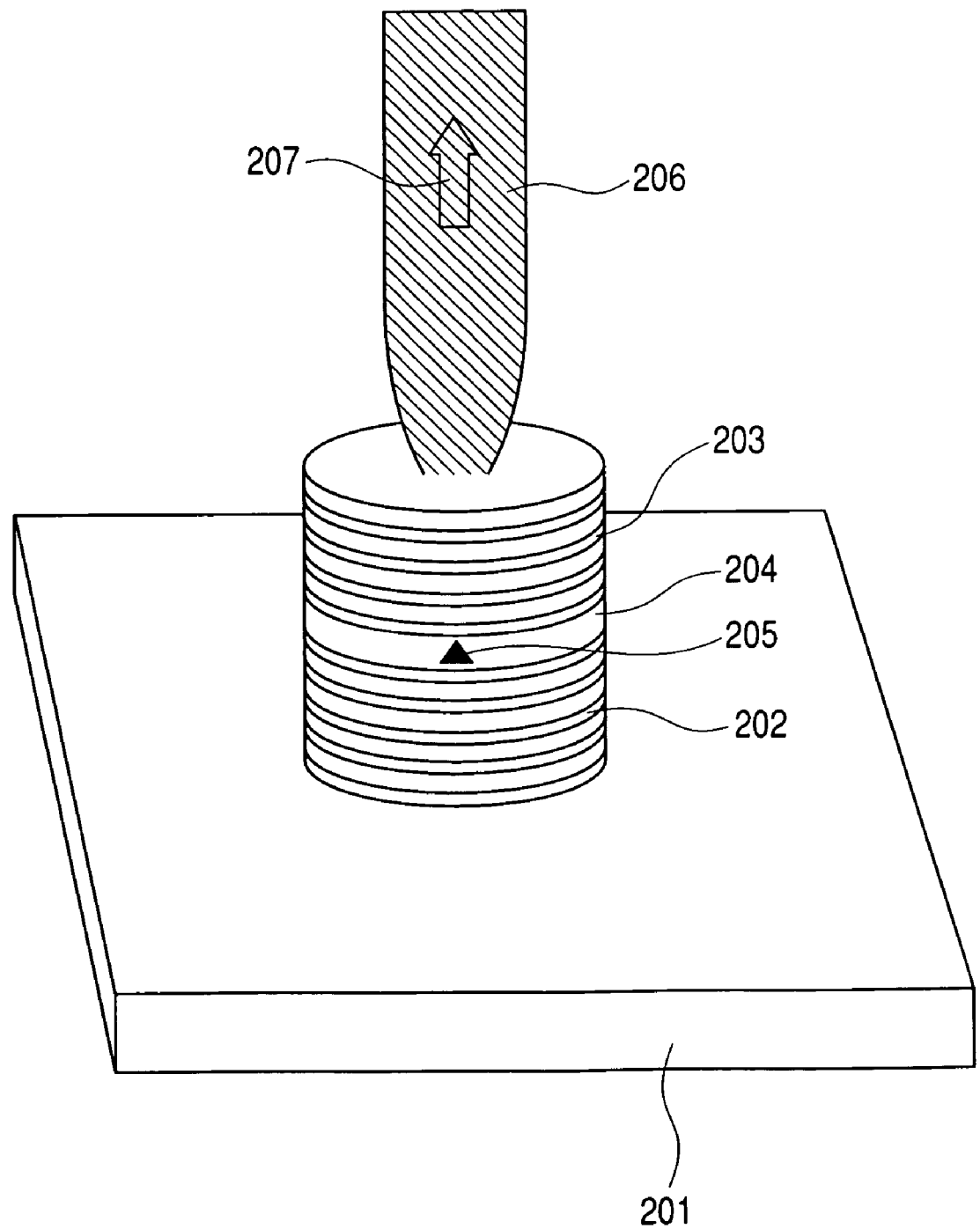
FIG. 2 is a schematic view showing the specific configuration of a microcavity LD according to Example 1.

FIG. 2 shows the microcavity LD used in the present example. FIG. 2 schematically shows the appearance of a cylindrical microcavity LD. The microcavity LD is constituted of a micro-optical cavity, which includes mirrors 202 and 203 for first and second micro-optical cavities and a cavity spacer 204 on the substrate 201, and an active layer 205. The micro-optical cavity has a size permitting a small region for confining light to have a size corresponding to the wavelength of the light. Reference numeral 206 denotes an emitted laser beam. An arrow 207 denotes a direction of emission, that is a light-emitting direction.

In the cylindrical microcavity LD, light is confined by the multilayer mirrors 202 and 203 in the light-emitting direction and total internal reflection caused by a difference in refractive index between a cylinder and the outside in the normal direction of the side of the cylinder, the normal direction being perpendicular to the light-emitting direction. Such a cylindrical microcavity has a high Q-factor of 1000 or more that indicates the quality of confinement.

The inside of the cavity spacer 204 includes the active layer 205 for emitting light. An example of an active substance and an active structure of the active layer includes a high-efficiency optical semiconductor (direct-band gap semiconductor) of a quantum dot, a quantum well and so on. For example, the quantum dot is made of InAs and is formed by a method including a self-assembling method called SK growth method or a process including lattice distortion caused by lattice constant mismatch and a break and reconfiguration during crystal growth such as MBE.

Wiring is provided (not shown) to inject carriers of electrons and a positive holes into the active layer. The wiring is connected to a power supply for supplying current. The active layer 205 physically reacts to the current, operates as a laser due to the effect of the cavity, and outputs the laser beam 206.

According to recent basic research, an active layer is confined in a semiconductor microcavity which has high quality, that is a high Q-factor and has a size corresponding to a wavelength, so that light emission is limited and coupling is made highly efficiently to the single light mode of the cavity. As a result, a laser with an untralow threshold value is achieved (Japanese Patent Application Laid-Open No. 10-284806).

Such an ultralow-threshold laser is sometimes called a zero-threshold laser. In an ordinary laser, a light-emitting property of an LED which is slow in response to low-current input is substantially absent. Even in a low-current region, it is possible to effectively use a plurality of characteristics of laser beam output, the characteristics including (1) response linearity of light output, (2) low noise and (3) high coherence that are highly advantageous when light output is used to transmit information.

A typical threshold input current of such a zero-threshold laser ranges between nA order and μA order.

In the present example, the LDs disposed in the channel LD layer 101 are changed in light emission responsively to conditions in the close channels.

The present example detected a change in the degree of the photoelectromagnetic field mode based on two environmental conditions of (1) a refractive index condition depending upon a concentration of a detected substance which is included in a fluid flowing into a channel and (2) a refractive index condition depending upon a temperature change caused by heat of reaction of a reactant which is included in a fluid flowing into a channel. Namely, (1) in the case of a high concentration or (2) in the case of a high temperature, the fluid is increased in refractive index and is reduced in difference in refractive index from a cylindrical cavity. Thus, the condition of confining light in the cylindrical cavity, that is the eigen mode of an electromagnetic wave is changed, changing the light output of the LD.

When a refractive index is largely changed, a threshold value increases to supplied current or more and light emission is stopped. Therefore, when the light-emitting states of the LDs are detected by the light-receiving layer 103, it is possible to measure the conditions of the channels close to the LDs. By properly designing the channels and the LDs regarding a substance to be applied, a place to be supplied with the substance, a place should be detected, and so on, thereby achieving an apparatus which is highly functional as a comprehensive and parallel detection system. Optically pumped lasers can be used as a LD.

Example 2

Figure 3A:
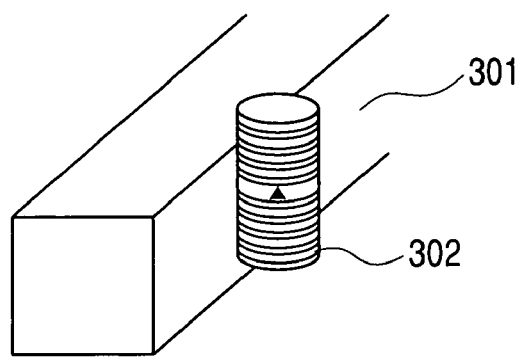
FIGS. 3A, 3B, 3C, 3D, 3E and 3F are schematic views each showing the configuration of a sensor device using a microcavity LD of Example 2.
Figure 3B:
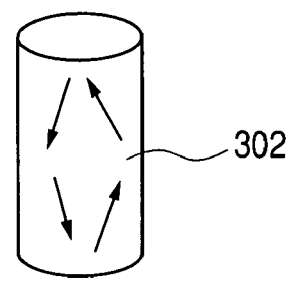
Figure 3C:
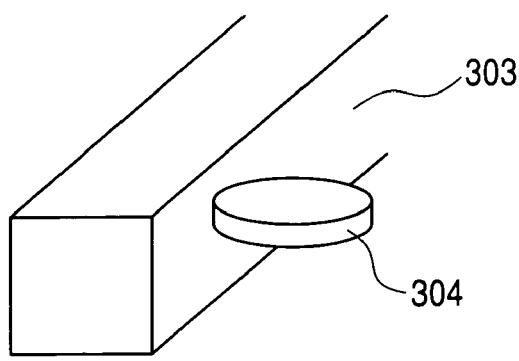
Figure 3D:
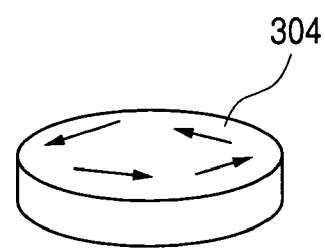
Figure 3E:
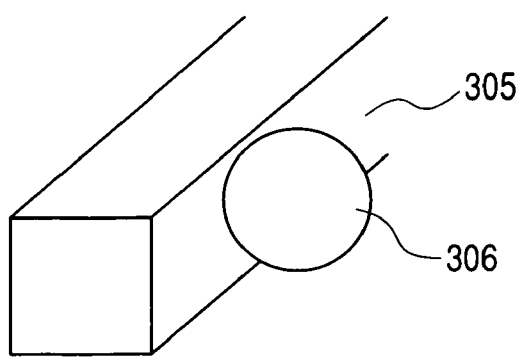
Figure 3F:
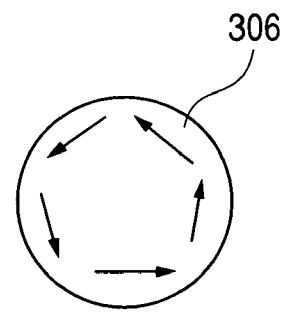

In contrast to Example 1, Example 2 of the present invention employs different forms for LDs and channels. Referring to FIGS. 3A to 3F and 4A and 4B, the present example will be described below. FIG. 3A shows the configuration used in Example 1. A cylindrical microcavity LD 302 is disposed so as to make contact with a channel 301. Arrows in FIG. 3B schematically show the eigen mode of light geometrically.

In the present example, a microdisk cavity LD 304 and a microdisk cavity LD 306 shown in FIGS. 3C, 3D, and 3E, and 3F are used instead of the cylindrical microcavity LD 302. In FIGS. 3A to 3F, reference numerals 303 and 305 denote channels. Light in the microcavities LD of FIGS. 3C and 3E have eigen modes which are geometrically shown in FIGS. 3D and 3F. Light propagates along a peripheral optical path which is known as a so-called whispering gallery mode (WGM) and is confined into a small region corresponding to a wavelength by total internal reflection.

Figure 4A:
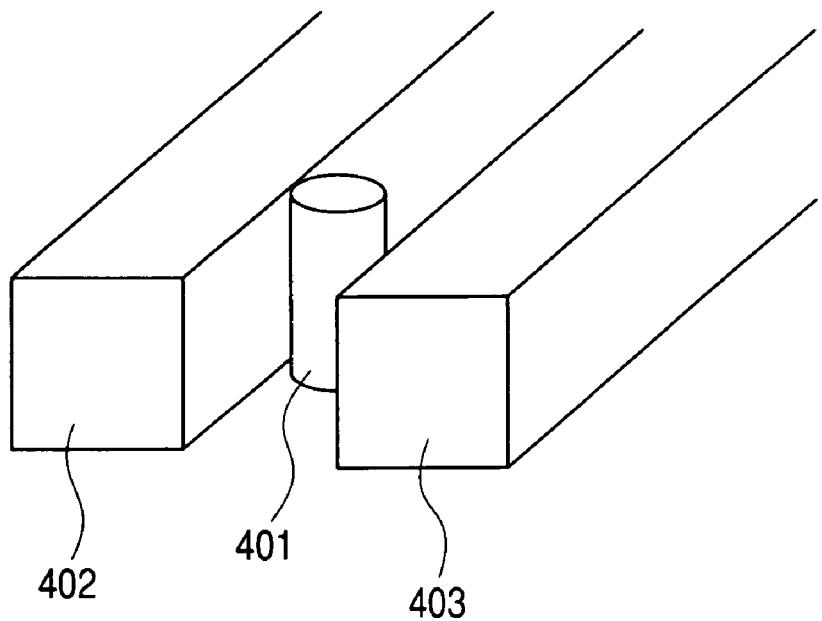
FIGS. 4A and 4B are schematic views showing another configuration of the sensor device using the microcavity LD of Example 2.
Figure 4B:
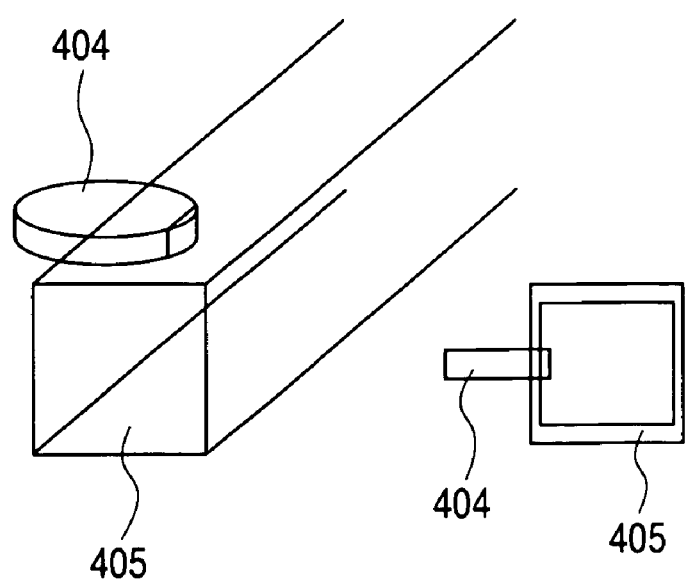

FIGS. 4A and 4B show embodiments in which contacts with channels are changed for a cylindrical microcavity, a microdisk cavity, and a microsphere cavity. FIG. 4A is a diagram schematically showing a LD 401 making contact with channels 402 and 403 at the same time. FIG. 4B is a schematic view showing a configuration in which a hole is formed on a channel 405 and a part of a cavity LD 404 is used as the wall of the channel. In FIG. 4A, it is possible to detect a sum of two or more channels and an average condition, achieving more stable detection and so on. In FIG. 4B, the cavity is directly in contact with a fluid, achieving highly sensitive detection.

Example 3

In Example 3 of the present invention, a pressure of an analyte flowing into a channel or a collision of a substance are detected. Referring to FIGS. 5A to 5D, Example 3 will be described below.

Figure 5A:
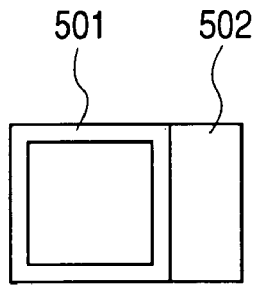
FIGS. 5A, 5B, 5C and 5D are schematic views showing the configuration of a sensor device using a microcavity LD of Example 3.
Figure 5B:
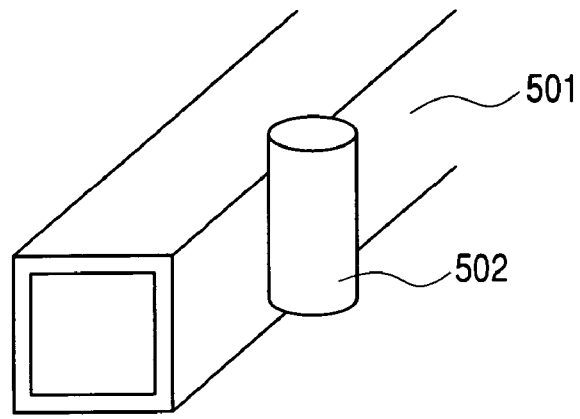
Figure 5C:
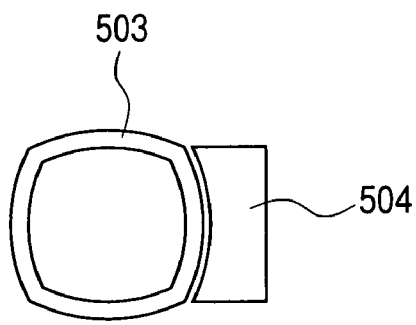
Figure 5D:
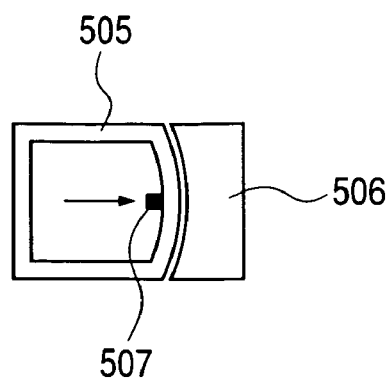

FIG. 5B is a schematic view showing that a microcavity LD 502 makes contact with a channel 501 as Example 1. FIG. 5A is a sectional view of FIG. 5B. FIG. 5C is a sectional schematic view showing that a fluid in the channel increases in pressure and thus a channel 503 is expanded and deformed. A microcavity LD 504 making contact with the channel deformed thus is also deformed by force applied from the channel. The confinement of light in the microcavity, that is the space mode of an electromagnetic wave highly depends upon a boundary condition. Thus, deformation on the cavity changes confinement of light. With the above change, the light emission of an LD is changed according to an oscillating condition of a laser. Hence, by detecting a change in light emission, it is possible to detect a small change in the pressure of the channel. FIG. 5D shows an example for measuring the quantity, speed, mass and so on of a detected substance particle 507 when the detected substance particle 507 having a relatively large mass is mixed in a fluid flowing into a channel 505. In this case, when the substance collides with the wall of the channel 505, the wall of the channel is deformed by reaction impulse resulting from a relatively large change in kinetic momentum. A microcavity LD 506 making contact with the channel is deformed according to the deformation and changes the light emission of the LD as in the example of pressure detection shown in FIG. 5C.

Since an amount of deformation depends upon multiplying effect of a collision frequency, a colliding speed, and a mass of a collided substance. Thus, by detecting the light emission of the LD, it is possible to measure a quantity, a speed, and a mass of the detected substance particle 507.

Example 4

Figure 6A:
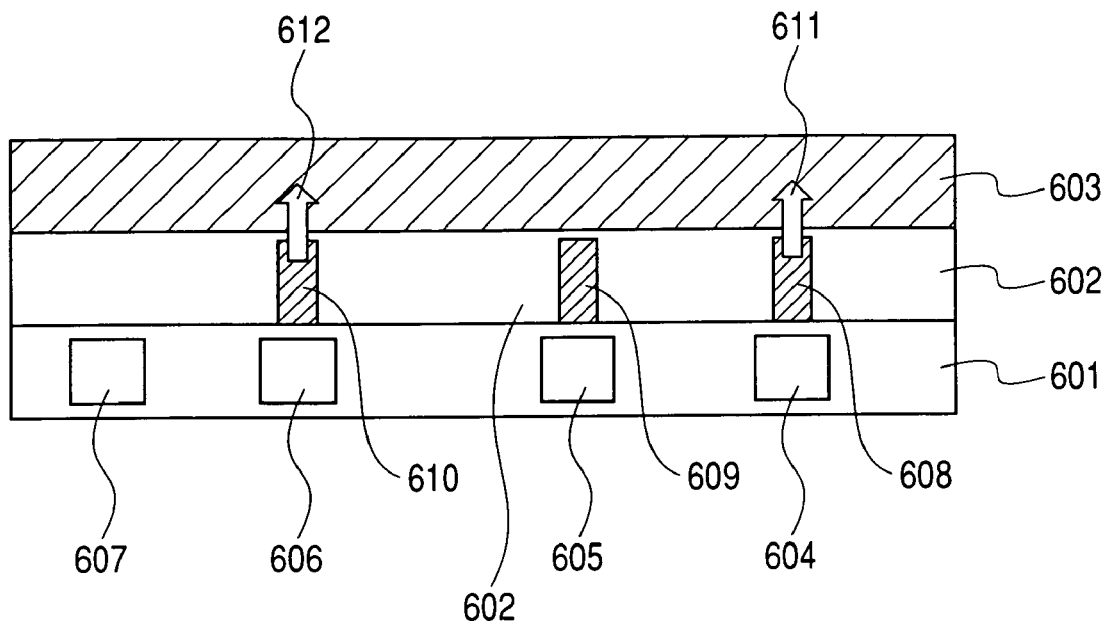
FIGS. 6A and 6B are schematic views showing the configuration of a sensor device using a microcavity LD of Example 4.
Figure 6B:
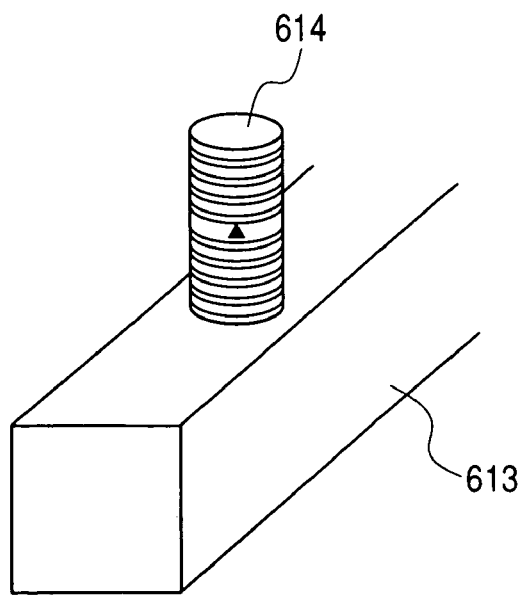

Referring to FIGS. 6A and 6B, Example 4 of the present invention will be described below.

FIG. 6A is a schematic view showing the configuration of a sensor device in cross section. In the present example, the sensor device is constituted of three layers of a channel layer 601, an LD wiring layer 602 having microcavity LDs, and a light-receiving layer 603. Reference numerals 611 and 612 denote light output.

As schematically shown in FIG. 6B, cylindrical microcavity LDs 608, 609 and 610 are in contact with channels 604, 605 and 606 on the undersurfaces of cylinders. In FIG. 6B, reference numeral 613 denotes a channel and reference numeral 614 denotes a microcavity LD. Confinement of light in the axial direction of the cylinder is mainly caused by reflection of a multilayer film. In the present example, the number of layers is reduced in the multilayer film so as to be affected by the channels and a reflectivity is somewhat reduced, thereby optimizing interaction with the channels. Further, in FIG. 6A, reference numeral 607 denotes a channel and a microcavity LD does not make contact with the channel in the cross section of the sectional view. FIG. 6A shows that 608 and 610 of the plurality of disposed microcavity LDs emit light according to the conditions of the channels with which the undersurfaces of the microcavity LDs are in contact and the microcavity LD 605 does not emit light. Light emission was detected by the area sensor of the light-receiving layer 603. A CCD is used as the area sensor. Another most suitable sensor such as a CMOS image sensor may be used in consideration of power consumption.

When the layer having the channels and the layer having the LDs are separated from each other, while optimization of a multilayer mirror becomes somewhat complicated, the manufacturing process becomes more simple due to the separated layers.

Example 5

Figure 7A:
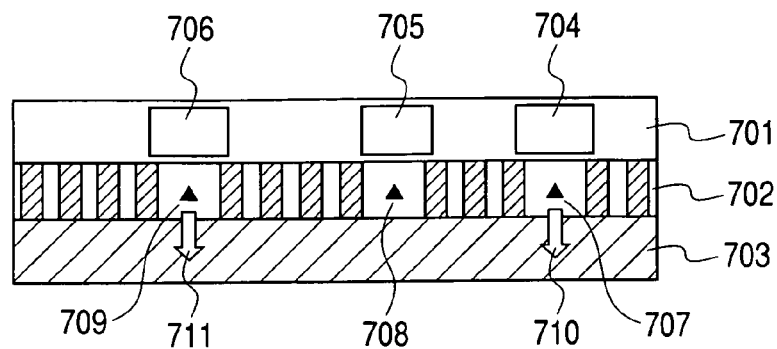
FIGS. 7A, 7B and 7C are schematic views each showing the configuration of a sensor device using a microcavity LD of Example 5.
Figure 7B:
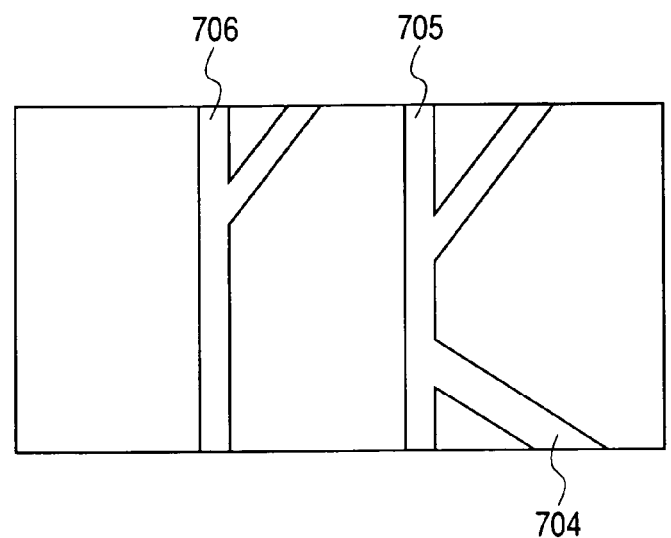
Figure 7C:
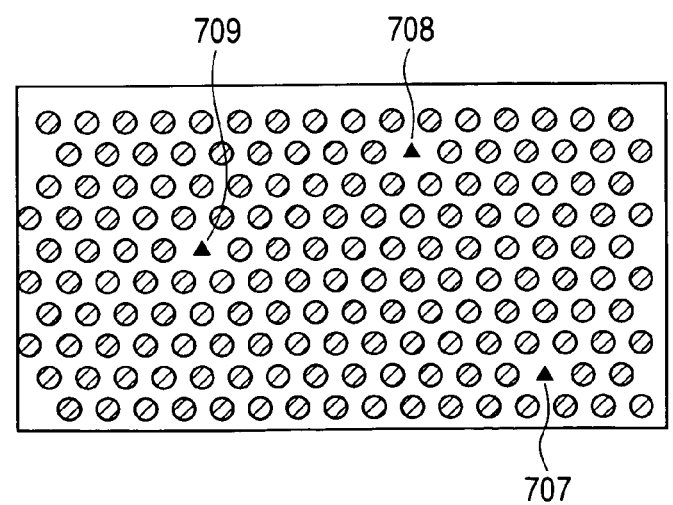

Referring to FIGS. 7A, 7B and 7C, Example 5 of the present invention will be described below. In the present example, a so-called Photonic Band Gap (PBG) structure is used as a microcavity LD. FIG. 7A is a schematic longitudinal section showing the configuration of the present example. An LD layer 702 including PBG cavities is disposed while making contact with a channel layer 701 including channels 704, 705 and 706. Further, a light-receiving layer 703 is disposed to receiving light outputs 710 and 711 from the LDs.

FIG. 7B is a schematic plan sectional view showing the channel layer 701. FIG. 7C is a schematic plan sectional view showing the LD layer 702. The PBG is constituted of cylindrical holes which are shaded portions arranged regularly in FIGS. 7A and 7C.

However, the regular arrangement of the holes includes microcavities represented as 707, 708 and 709, on which holes are not disposed. As a result, periodicity locally disappears. It is known that the local defects localize light and thus function as cavities. Since the size of the defect is determined by a wavelength, the defects caused by the absence of a small number of holes in the PBG are operated as microcavity LDs by injecting therein an active substance for emitting light. In this example, an active substance indicated by black triangles is injected into the microcavities 707, 708 and 709 which are connected to a power supply for carrier injection via wiring (not shown).

Light emission is changed by interaction with the channels on the same principle as those of the other examples.

In the case of the PBG microcavity LD according to the present example, light is confined according to periodicity in the in-plane direction and light is confined by total internal reflection caused by a difference in refractive index in the thickness direction, that is in the direction of the normal to a surface where the cavity LD and the channel are in contact with each other. Thus, light emission is modulated by a change in refractive index which depends upon the temperature and concentration of the channel, achieving detection.

The periodical length of the PBG, the size of the channel and so on are not limited to FIGS. 7A, 7B and 7C. The periodical length and so on can be adjusted properly in view of a design parameter such as a light wavelength depending upon the used active substance.

Example 6

Figure 8:
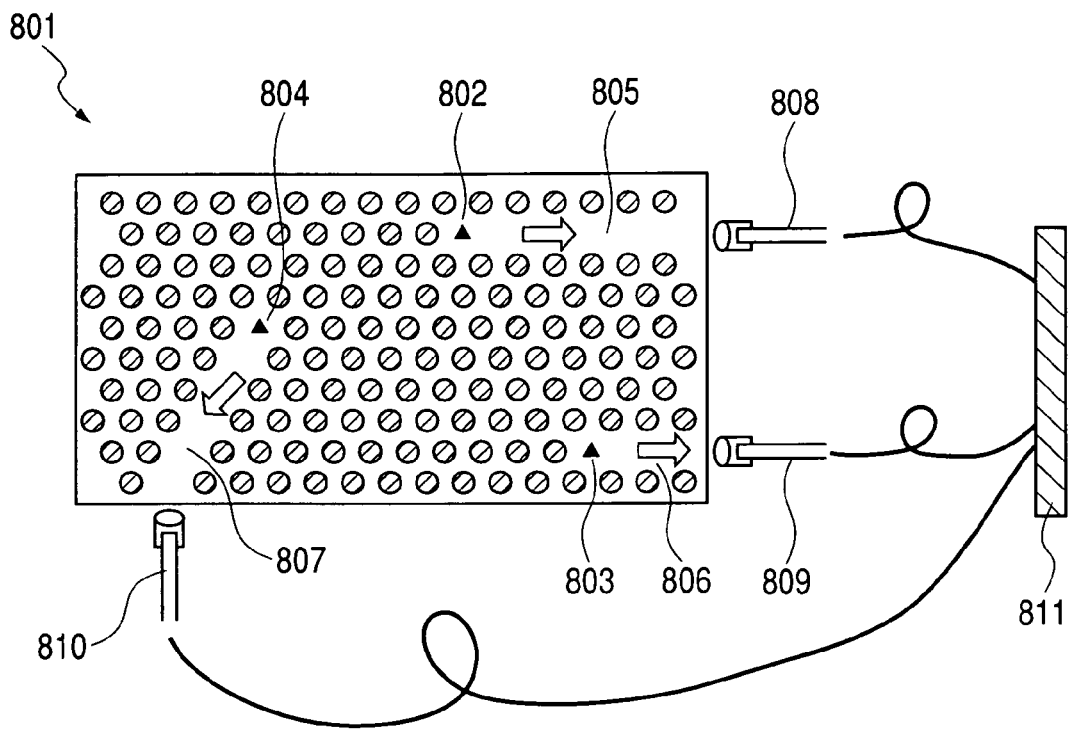
FIG. 8 is a schematic view showing the configuration of a sensor device using a microcavity LD of Example 6.

Referring to FIG. 8, Example 6 of the present invention will be described below.

As with Example 7, the present example constitutes microcavity LDs 802, 803 and 804 and the cross section is fundamentally similar to FIGS. 7A, 7B and 7C of Example 7. However, as shown in FIG. 8 which is a plan sectional view showing an LD layer 801, a local defect in PBG is formed not only on a cavity but also on a waveguide and light output is developed in the in-plane direction and is detected through an end face of the layer in the present example.

It is known that a periodic hole is made absent so as to connect the waveguide like a straight line or a curve and thus light can be propagated even when the size is equal to or smaller than a wavelength. Light having been guided by in-plane waveguides 805, 806 and 807 configured thus and have reached the end face is inputted to a fiber via coupling lenses 808, 809 and 810. Light inputted to the fiber is optically connected to a predetermined position of a photo detector 811 and is detected. Thus, it is possible to detect a PBG microcavity LD having emitted light and a quantity of the emitted light. Therefore, it is possible to detect various conditions of channels making contact with the PBG microcavity LD.

The light-receiving element is disposed separately in this arrangement, which is an advantage to a configuration where two or more combinations of channels and PBG layers are laminated and integrated or the channels are caused to penetrate the PBG layer and are connected to each other.

Besides, a surface for taking out light output is not strictly limited to an end surface. The arrangement can be freely changed as long as the object of the present invention is achieved. For example, light temporarily travels in the in-plane direction from a cavity LD. Thereafter, light is reflected and propagated in the thickness direction while a reflection plane and so on is provided, and the light is taken out in the thickness direction.

Further, an active substance selected from the group consisting of Er and Tm is provided not only on the cavity but also a waveguide to perform light amplification, so that light output is amplified and thus an SNR is improved. Such a change is also effective in the present invention.

Example 7

Figure 9:
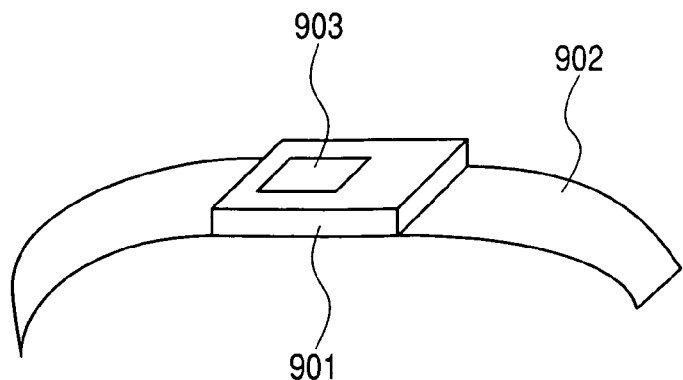
FIG. 9 is a schematic view showing the configuration of a mounted sensor device using a microcavity LD of Example 7.
Figure 10:
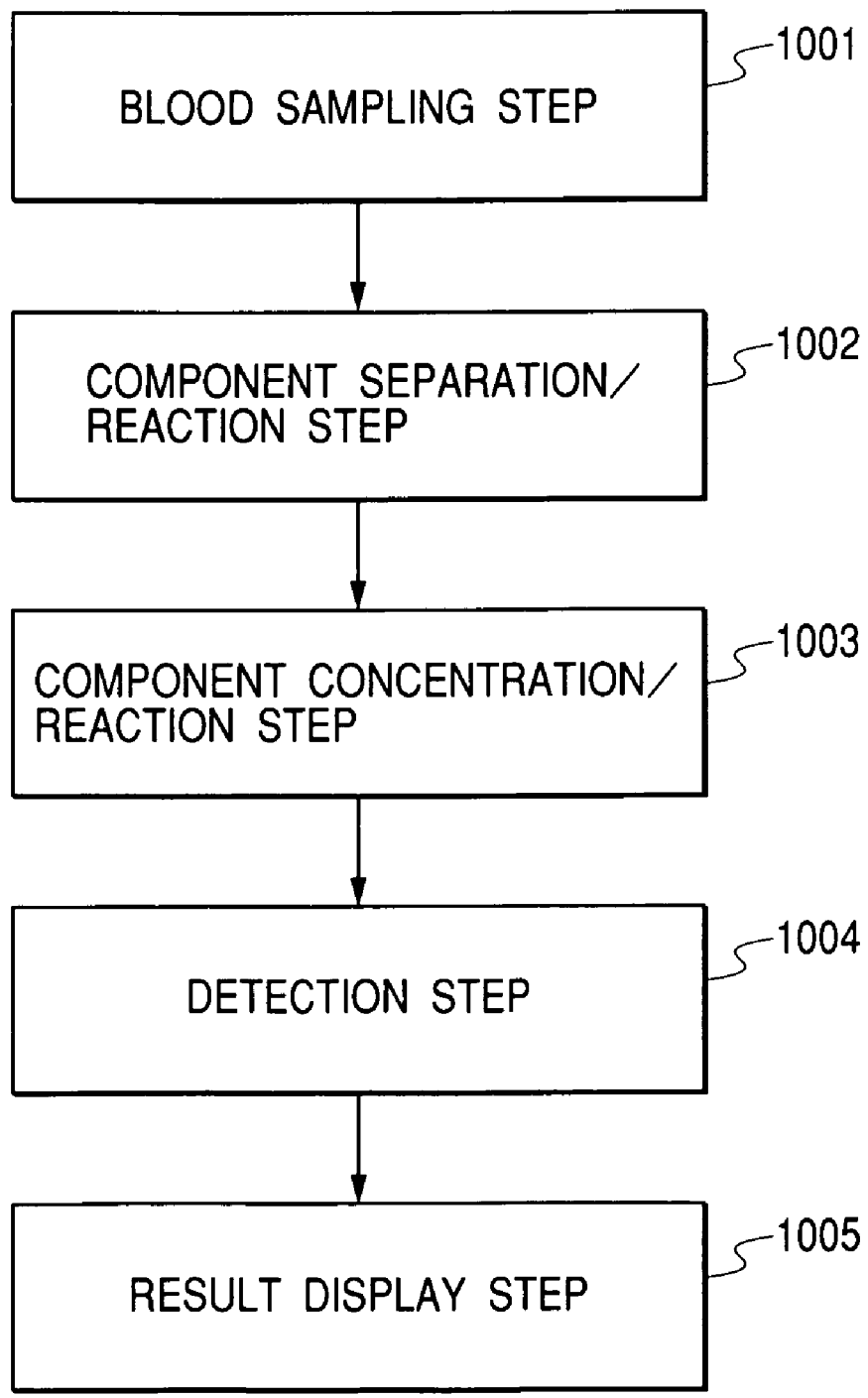
FIG. 10 is a schematic view showing the steps of a sensor device using the microcavity LD of Example 7.
Figure 11:
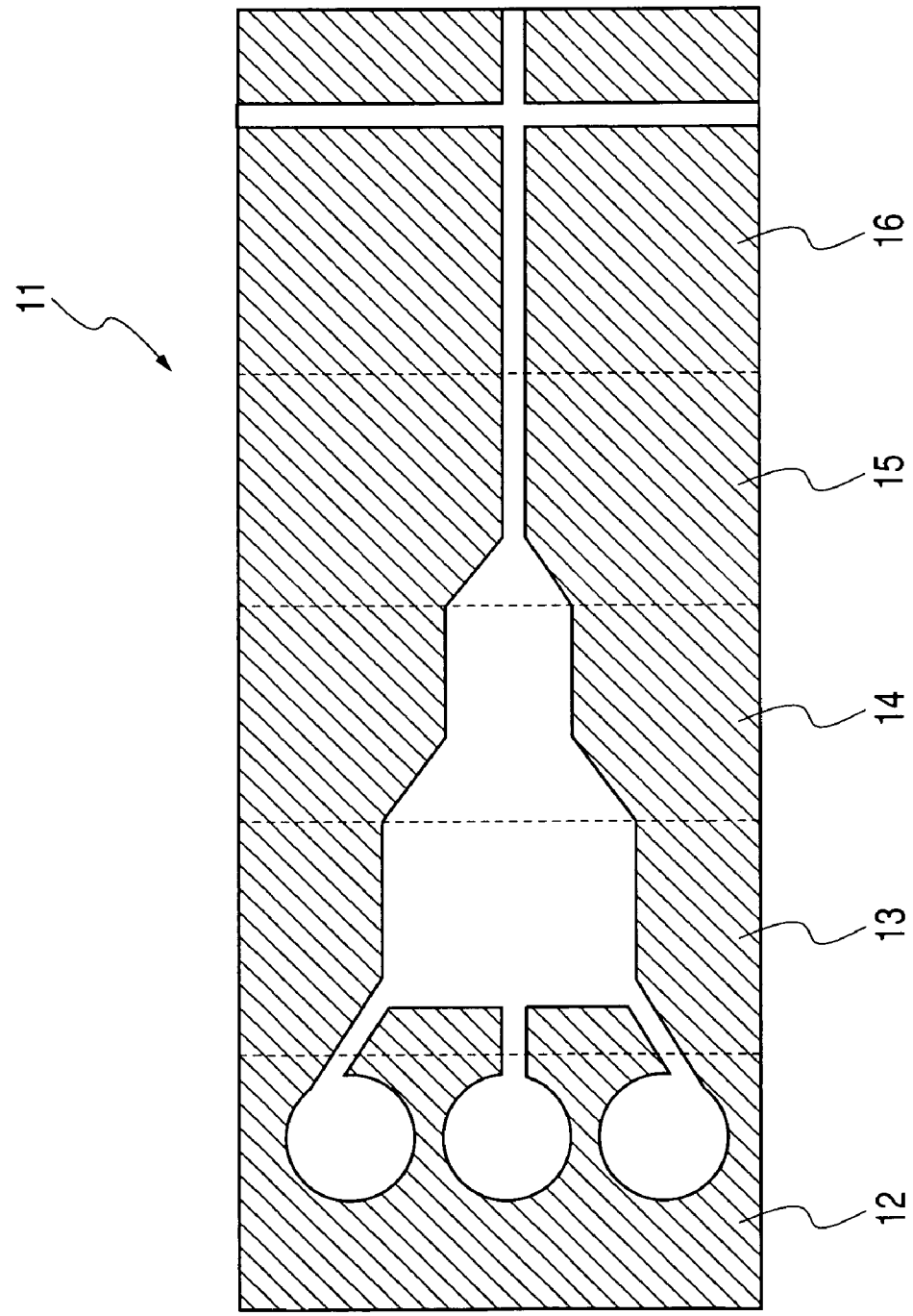
FIG. 11 is a conceptual view showing a conventional microreactor.

Referring to FIGS. 9 and 10, Example 7 of the present invention will be described below.

FIG. 9 shows a detector including the configuration of microcavity LDs and channels according to the present invention. FIG. 9 is a schematic view showing that the detector is formed like a watch and is attachable onto a human arm.

The detector is attached onto the arm by a belt 902. Necessary information is detected by a sensor 901 from illustrated steps including blood sampling. A detection result is displayed on a display 903.

FIG. 10 shows a flow only including representative steps for detecting necessary information. The series of steps is constituted of a blood sampling step 1001 for sampling a small amount of blood from a human body by using a collecting needle (not shown), a component separation/reaction step 1002 for separating a target component from the components of blood and causing a reaction required for separation, a component concentration/reaction step 1003 for increasing a detection sensitivity, a detection step 1004 for bringing a fluid, which contains a detected substance having been concentrated, into contact with the microcavity LD of the present invention so as to perform high-sensitive detection and converting a detection result directly into a desired detection result by calculation, and a result display step 1005 for transmitting the result to the display 903 to provide a display of the result.

As shown in FIGS. 9 and 10, a portable detector and tester can be formed by using the microcavity LDs and channels of the present invention. Needless to say, the attaching type device of the present example may properly comprise a communicating function to a server or the like, a clock, and a photographing function of a portable terminal.

The present invention is not limited to the above-described examples and a sequence and so on may be changed without departing from the spirit of the present invention.

Example 8

The present example will describe one form where the sensor of the present invention is applied as a biochemical sensor using specific binding such as an antigen-antibody reaction. The following explanation will be made in accordance with FIGS. 12A, 12B and 13.

Figure 12A:
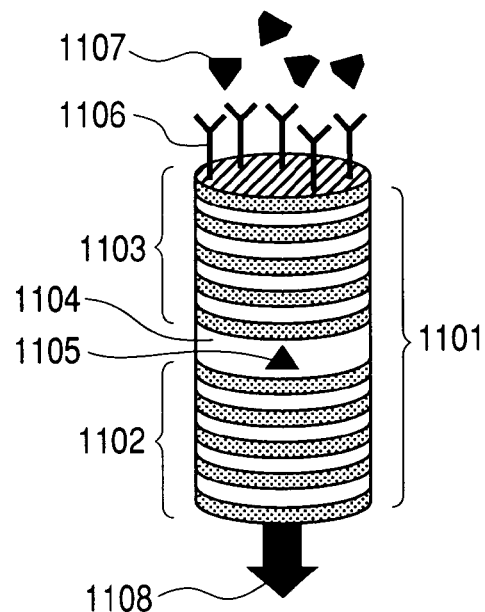
FIGS. 12A and 12B are schematic views showing the configuration of a biochemical sensor using a microcavity LD of Example 8.

FIG. 12A shows a cylindrical microcavity laser 1101. The laser is constituted of a multilayer mirrors 1102 and 1103, a cavity spacer 1104, and a laser medium 1105. Surface modification is performed on the outer surface of the multilayer mirror 1103 to fix ligands 1106, so that a biochemical sensor is formed.

An analyte 1107 serving as a detected substance is contained in, for example, a fluid and is carried close to the sensor of the present example, and the analyte 1107 is specifically bound to the ligands 1106. The binding changes the characteristics of the multilayer mirror 1103. Such a change includes some phenomena such as a change in the permittivity and refractive index of a multilayer film substance due to a change in an electronic state on a surface of a multilayer film, and a change in the optical thickness of the multilayer film due to the adhesion of a substance simply having a different refractive index from that of an atmosphere. However, a change in the optical characteristics of the multilayer mirror is the essence of the present example. Such a change varies the light-confining state of the microcavity and thus the characteristics of the microcavity laser are changed. Namely, states such as a threshold value and the oscillation mode of laser oscillation are changed.

In this way, the oscillation state of the laser is changed by specific binding. Thus, by setting laser oscillation at around the threshold value, coupling does not occur as shown in FIG. 12A.

In the initial state, laser oscillation occurs and laser output light 1108 is emitted to the outside. As show in FIG. 12B, in a state after coupling, a laser threshold value is increased by a change in the light confinement of the microcavity LD and laser oscillation does not occur, so that laser output light is not emitted. In this way, laser output light is varied according to the presence or absence of coupling of the analyte, which serves as a detected substance, to the ligands. Thus, it is possible to detect the presence of the analyte and a coupling state.

Additionally, the initial state indicates the state of the microcavity laser after the modification of the ligands. A setting is made which includes a change in the modification of ligands.

Moreover, in the present example, laser oscillation occurs in the initial state. This process may be reversed. Namely, the following setting is also applicable: laser oscillation does not occur in the initial state but laser oscillation occurs after the analyte is coupled. It is needless to say that selection can be performed according to the design of a sensor system.

Meanwhile, in order to increase a detection sensitivity, the following change is also applicable: an analyte is properly labeled with a metal and a permittivity is largely changed when coupling is made with ligands. Such a change can be properly selected according to the use and specification of the sensor system.

Figure 13:
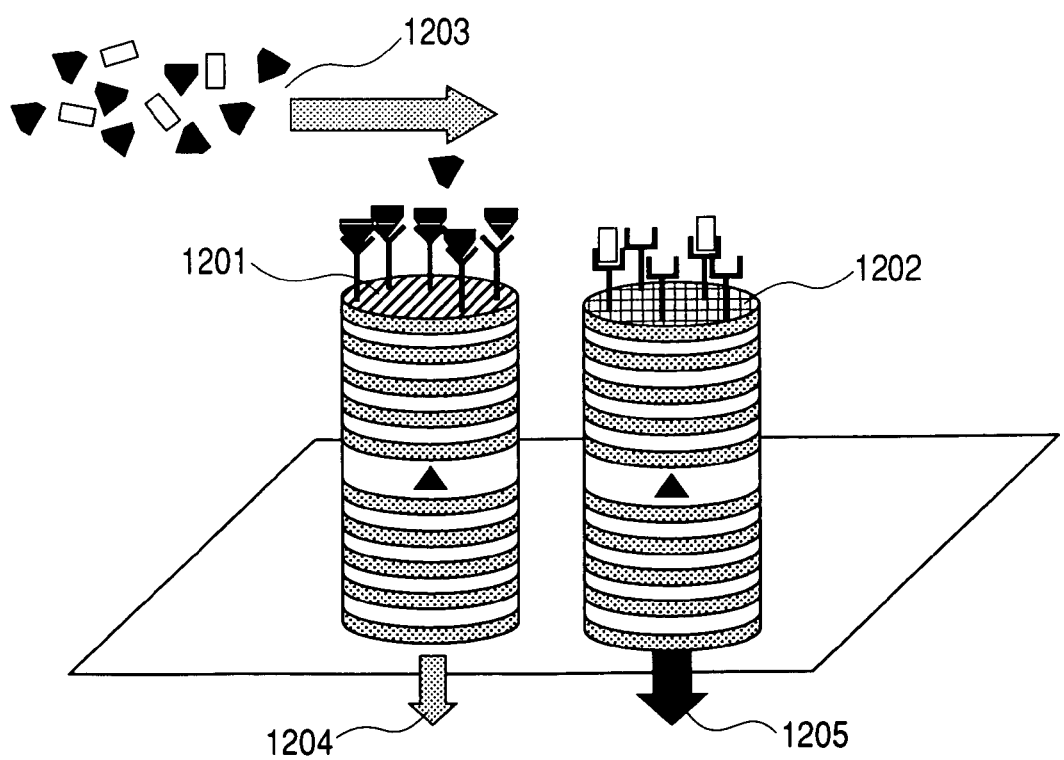
FIG. 13 is a schematic view showing an example of another embodiment of a biochemical sensor according to Example 8.

Further, as shown in FIG. 13, a plurality of laser sensors having ligands modified according to the present example may be arranged on a substrate. Reference numerals 1201 and 1202 denote the modified portions of ligands of a first kind and a second kind. In the case where the arrangement is constituted of sensors having two or more kinds of modified legands, when a fluid 1203 containing two or more kinds of mixed analytes is carried close to the sensors, each of the analytes is specifically bound to the sensor having the corresponding ligand. As indicated by 1204 and 1205 of FIG. 13 in a simulated manner, laser output light from the sensor is varied with the kinds of an analyte-ligand pair. Therefore, the sensor position is kept track for each kind of ligands and the position of different laser output is detected by using, for example, a sensor of an area type, so that two or more kinds of analytes can be readily detected in a collective manner.

Figure 12B:
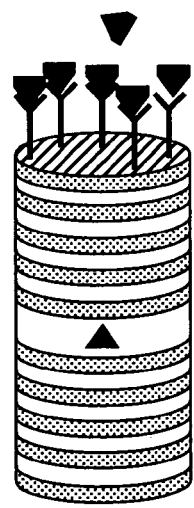
Figure 14A:
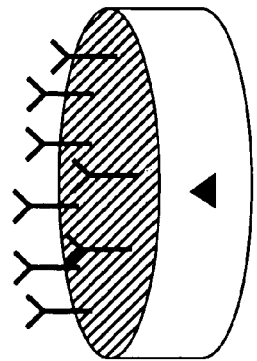
FIGS. 14A, 14B, 14C and 14D are schematic views showing another embodiment of the biochemical sensor according to Example 8.
Figure 14B:
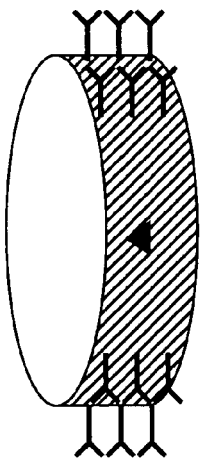
Figure 14C:
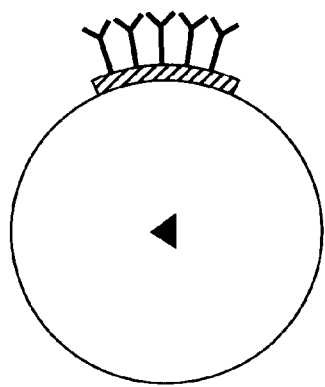
Figure 14D:
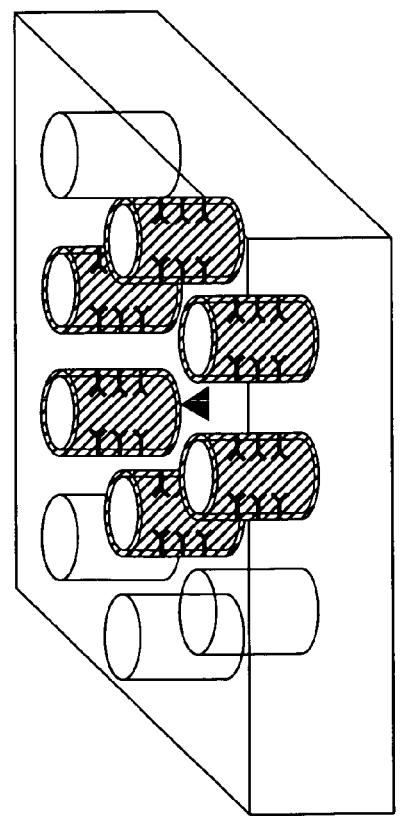

As shown in FIGS. 12A, 12B and 13, the microcavity LD of Example 8 is cylindrical. It is needless to that the microsphere cavity (FIG. 14A), the microdisk cavity (FIGS. 14B and 14D), a photonic crystal point defect cavity (FIG. 14C) and so on can be used properly.

Additionally, in the sensor of the present example, two or more kinds of ligands can be modified on a single microcavity. The effect will be discussed below.

Figure 15A:
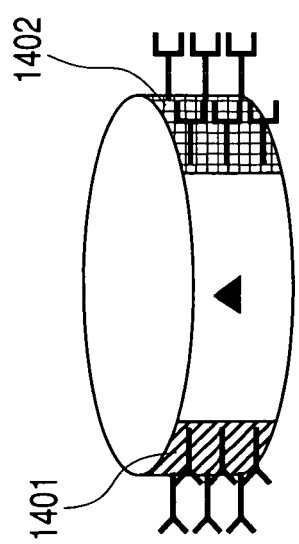
FIGS. 15A, 15B and 15C are schematic views showing the configuration of a biochemical sensor according to Example 9.
Figure 15B:
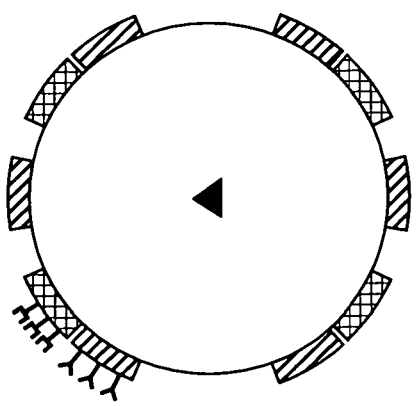
Figure 15C:
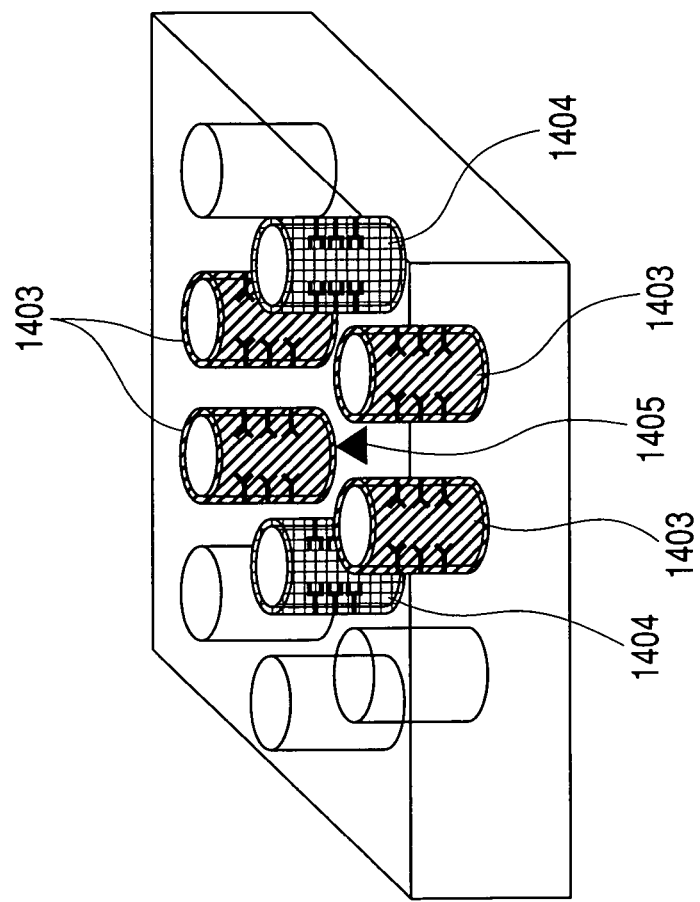

A laser normally has a plurality of laser oscillation modes where oscillation may occur, and the microcavity LD also has such a plurality of laser oscillation modes. Particularly in the case of highly symmetric spheres and disks or photonic crystals, a plurality of degenerate modes are available. As shown in FIG. 15, when a plurality of ligand modifications are performed in the plurality of laser oscillation modes so that symmetry is lost and degeneracy is lifted for each kind of ligands. Thus, laser oscillation has different modes due to the specifically bound analyte. For example, a hexagonal ligand modification 1401 and a square ligand modification 1402 are provided in FIG. 15B. In FIG. 15C, around a photonic crystal point detect 1405 of a cylindrical hole called a triangle lattice structure, four cylindrical holes 1403 and two cylindrical holes 1404 are disposed. A first ligand modification is performed on the inner wall of the cylindrical hole 1403 and a second ligand modification is performed on the inner wall of the cylindrical hole 1404. The sensor composed of the microcavity LD configured thus has a different laser oscillation mode according to the kind of the specifically bound analyte. Therefore, a Q-factor (Quality Factor) corresponds to an oscillation mode, that is a threshold value is varied with different states of light confinement, so that a change in laser oscillation output is detected. Alternatively, the emitting state of oscillated laser output light, that is the orientation and intensity distribution of laser output light are detected by an area sensor, a divided detector and so on, thereby detecting a plurality of analytes.

Example 9

Example 9 shows an example indicating a configuration for locally increasing the sensitivity of a sensor according to the present invention.

Referring to FIGS. 16A and 16B, the principle of the present example will be described below.

In FIG. 16A, a dielectric 1501 corresponds to the inside of a microcavity, and light 1502 confined inside travels to an interface. High-efficiency confinement of light in a microoptical cavity depends upon total internal reflection of an interface between a substance of a high refractive index and a substance of a low refractive index expect for a part using a periodic structure of a multilayer film or a photonic crystal. FIG. 16A shows that the light 1502 is totally reflected on the interface. Reflected light 1503 with a reflectivity of 100% is theoretically obtained. In this case, as has been widely known, a displacement 1504 called Goos-Hänchen shift occurs as a geometrical-optical path on a reflecting position. The size of the shift 1504 is an order of a used light wavelength. Hence, it is understood that a measurement range is almost a used light wavelength when the environments of the microcavity LD are measured by the microcavity LD of the present invention. Further, it is understood that an interaction length is also an order of a light wavelength when light interacts with a detected substance.

The present example shows an example of a configuration for performing detection with higher sensitivity. As shown in FIG. 16B, the configuration is characterized in that a metal thin film is disposed on an interface where a microcavity is adjacent to a detected substance. In FIG. 16B, a metal thin film 1506 is formed on an interface between a dielectric 1505 and the outside and thus total internal reflection is changed into a phenomenon for moving electrons in metal. The motion of electrons in metal is called surface plasmon particularly when a thin film or the like has an enhanced surface/interface effect. Then, light can propagate over a distance longer than a light wavelength around the interface of a metal thin film dielectric while light and metal surface plasmon interact with each other. Propagated light with the motion of electrons is called metal surface plasmon polariton. The present example uses a propagation distance of the polariton that is longer than a light wavelength. Namely, by using the propagation distance of polariton 1507 that is an effective interaction length with a detected substance, the sensitivity of the microcavity laser sensor of the present invention is increased.

As shown in FIG. 16C, an actual structural example indicates that corridor mode light 1509 of a microsphere cavity laser 1508 is propagated around a surface longer than ordinary total internal reflection by a metal thin film 1510 formed around a detected substance 1511, thereby increasing detection sensitivity.

Further, detection sensitivity can be locally increased by making the same change also in microcavity laser sensors having shapes other than the microsphere cavity. For example, as shown in FIGS. 17A and 17B, various arrangements can be properly made which include a metal thin film 1601 provided on the side of a cylindrical microcavity (FIG. 17A) and a metal thin film 1603 provided on the undersurface of a cylindrical microcavity (FIG. 17B). Besides, in FIGS. 17A, 17B and 17C, reference numerals 1602 and 1604 denote detected substances, reference numeral 1605 denotes photonic crystal substrates, reference numeral 1606 denotes periodic cylindrical holes, reference numeral 1607 denotes a laser medium, and reference numeral 1609 denotes a channel and a detected fluid.

Further, the metal thin film can have a concentric structure on the undersurface of a cylinder and thus light can be concentrated more at the center of the undersurface to increase a local detection sensitivity around the center.

Moreover, as shown in FIG. 17C, a point defect cavity of a photonic crystal can be also increased in detection sensitivity by making the same change. Particularly in the case of sensing on the micro-channel system according to Example 5 of the present invention, it is highly effective to locally increase a detection sensitivity around the channel. Thus, a channel cover 1608 and a metal thin film 1610 of FIG. 17C form a channel and the metal thin film. Combined with an increased interaction length of metal surface plasmon polariton, detection can be performed with higher sensitivity by causing the metal thin film to serve as a channel wall directly making contact with a fluid.

Example 10

Figure 18:
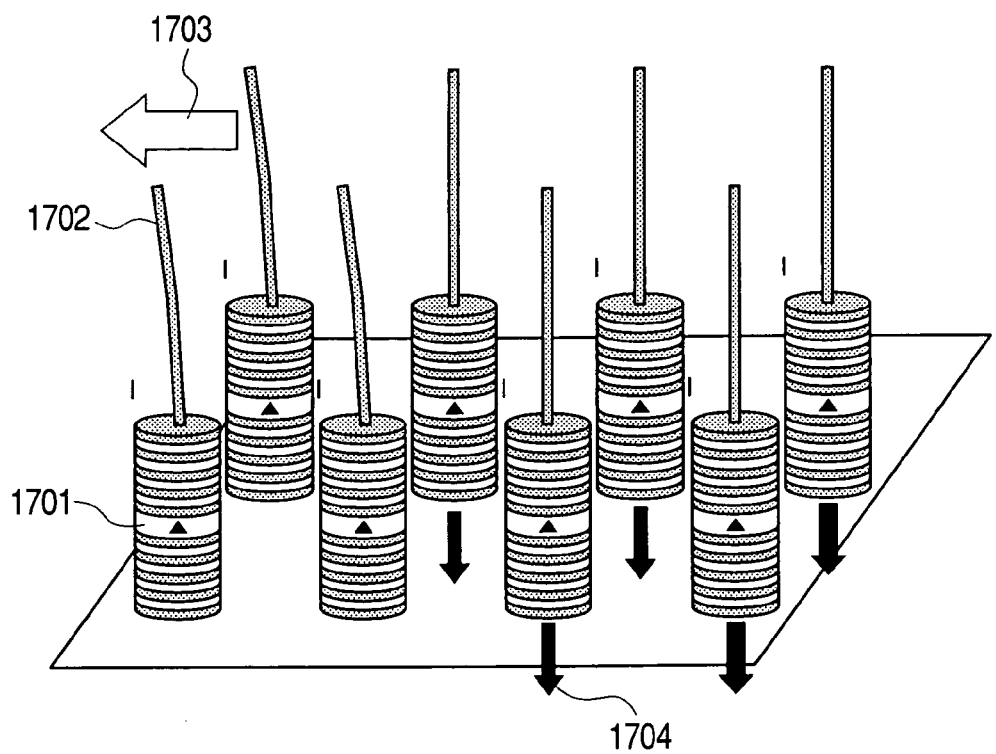
FIG. 18 is a schematic view showing an example of the configuration of a tactile sensor according to Example 11.

The present example indicates an example of the configuration in which the microcavity laser sensor of the present invention is applied to, for example, a mechanical sensor such as a tactile sensor for detecting a small mechanical change. In FIG. 18, eight cylindrical microcavity lasers 1701 are formed on a common substrate. The present example is characterized by tactile probes 1702, which are structures mechanically connected to the top surfaces of cylindrical microcavities. When mechanical force 1703 is applied to the tactile probe 1702, the probe 1702 is deformed and the cavity of the microcavity laser 1701 is deformed together with the probe. The light confinement of the microcavity depends upon its shape. Particularly in the case of a cavity used in the present invention with a high Q-factor, even a small change varies confinement of light and a mode of light. Therefore, as shown in FIG. 18, when force is applied to the three probes on the left end, deformation stops laser oscillation, laser oscillation output light is emitted, and only the other microcavity lasers can have laser oscillation output light 1704.

In this way, for example, a pressure distribution is detected as with tactile sense of a hair on a human skin and output light is detected by using an area sensor or the like, so that the pressure distribution can be obtained as an image in a collective manner. Moreover, since the configuration of the present example employs the presence or absence of laser oscillation and light output, the system has quite a high response speed and can be operated at, for example, MHz order or higher. Thus, a pressure distribution can be readily detected as a moving image in so-called real time and the system can be applied to a feedback system for humans.

Figure 19:
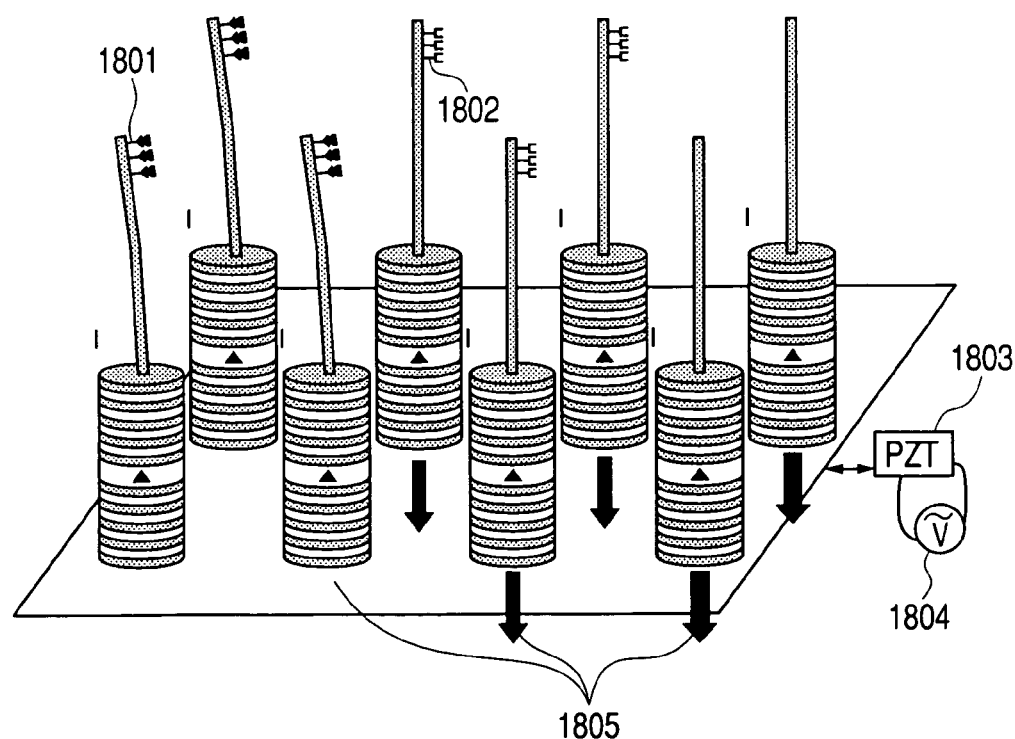
FIG. 19 is a schematic view showing an example of the configuration of a biochemical sensor using the tactile sensor according to Example 11.

In addition, it is needless to say that the sensor of the present example can be used for something other than a human body. For example, as shown in FIG. 19, ligands are modified on the tips of the probes. By using a change in mechanical response including a resonance frequency of the probe, the change being caused by the coupling of an analyte according to a weight of the analyte or a frictional resistance against ambient atmosphere, excitation modulation is performed by using a piezoelectric element actuator 1803 and a driving AC power supply 1804, a change in the output light 1805 is detected, and synchronous detection is performed as necessary, so that a substance can be detected with high sensitivity. In FIG. 19, reference numeral 1801 and a spare 1802 are tactile probes whose tips are modified with ligands of a first type and a second type. By using a specific binding of the ligand and the analyte, two or more kinds of substances are detected, the detection results are detected in parallel by an area sensor, and an image can be readily acquired from the results.

Additionally, the present example described ligand modification and specific binding. It is needless to say that detection can be performed by a more simple method which includes ordinary physical adsorption and a method using friction between a substance and a probe and a difference in viscosity between substances.

The invention claimed is:

1. A sensor for detecting information and outputting light according to the information, the sensor comprising:
a micro-optical cavity of a micro-activity laser configured to change a degree of selection of a photoelectromagnetic field mode according to an environmental condition of the micro-optical cavity; and
an active layer integral to the micro-optical cavity of the micro-cavity laser from which light emission is limited by influence of selection of a photoelectromagnetic field mode of the micro-optical cavity,
wherein the light emission is changed according to a change in the environmental condition and the information is detected by the change in light emission.

2. The sensor according to claim 1, wherein the sensor is disposed in a channel for flowing a fluid or near the channel.

3. The sensor according to claim 2, wherein enviromental condition is changed according to a solution flowing in the channel or a dissolved substance or solvent of the solution.

4. The sensor according to claim 3, wherein the channel is a microchannel having a dimension of 10 μm or more and a solution flowing in the channel forms a laminar flow on a predetermined position.

5. The sensor according to claim 3, wherein the enviromental condition is selected from the group consisting of a change in refractive index, light absorption, light scattering, a temperature change, and slight deformation of the micro-optical cavity of the sensor.

6. The sensor according to claim 5, wherein the change in refractive index depends upon a concentration of the solvent.

7. The sensor according to claim 5, wherein the change in refractive index depends upon a temperature of the solution.

8. The sensor according to claim 5, wherein the light adsorption depends upon a concentration of the dissolved substance.

9. The sensor according to claim 5, wherein the light scattering depends upon a concentration of the dissolved substance.

10. The sensor according to claim 5, wherein the temperature change is caused by heat generated by a chemical reaction of the solution and/or the dissolved substance.

11. The sensor according to claim 5, wherein the slight deformation of the sensors appears due to vibration caused by expansion and shrinkage resulting from a collision of the dissolved substance or a chemical reaction of a substance in the solution.

12. The sensor according to claim 5, wherein the slight deformation of the sensor appears due to a pressure change by expansion and shrinkage resulting from a change in a flow rate of the solution or a chemical reaction of a substance in the solution.

13. The sensor according to claim 1, wherein a surrounding part of the micro-optional cavity in the sensor is modified by an antigen or an antibody.

14. The sensor according to claim 1, further comprising a probe for generating mechanical deformation on the micro-optional cavity.

15. The sensor according to claim 1, further comprising a metal thin film between the micro-optical cavity and a detected substance.

16. A sensor array comprising a plurality of sensors, each according to claim 1 and collectively arranged juxtapositionally in a one- or two- dimensional array and outputting signals of juxtapositional light outputs from the sensors according to particular environmental information corresponding to the positions of each sensor.

17. A sensor using a microcavity laser having a micro-optical cavity and an active layer integral to the micro-optical cavity, wherein one of two supportingt substances capable of making specific binding with a substance to be detected is supported on a peripheral portion of the micro-optical cavity, and a specific binding state of the substance to be detected with the supporting substance is detected based on a laser oscillation state of detected laser light.

18. A sensor system, wherein the sensors of claim 17 are juxtapositionally arranged on a common substrate and plural kinds of substances to be detected are juxtapositionally detected by using a plurality of microcavity lasers juxtapositionally arranged.

19. The sensor according to claim 17, wherein a kind of a substance to be detected is detected according to a change in a laser oscillation mode of the microcavity, a peripheral portion of which supports plural kinds of the supporting substance, the supporting substances corresponding to plural kinds of the substance to be detected.

20. A sensor comprising a micro-optical cavity of a microcavity laser and a probe for generating mechanical deformation of the micro-optical cavity, wherein a state of the mechanical deformation is detected by measuring a change in laser oscillation state, the change being caused by deformation of the micro-optical cavity by the probe.

21. The sensor according to claim 20, wherein the probe supports one two supportig substances capable of making specific binding with the substance to be detected, and modulation of mechanical deformation of the micro-optical cavity through the probe is detected from a change in the laser oscillation state, which change is based on a resistance against ambient fluid and/or a change in weight of the probe by the specific binding.

* * * * *